US012036046B2

(12) United States Patent
Yahil

(10) Patent No.: US 12,036,046 B2
(45) Date of Patent: Jul. 16, 2024

(54) GATING OF MEDICAL IMAGING DATA

(71) Applicant: Siemens Medical Solutions USA, Inc., Malvern, PA (US)

(72) Inventor: Amos Yahil, Stony Brook, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 332 days.

(21) Appl. No.: 17/595,322

(22) PCT Filed: Sep. 5, 2019

(86) PCT No.: PCT/US2019/049681
§ 371 (c)(1),
(2) Date: Nov. 15, 2021

(87) PCT Pub. No.: WO2021/045760
PCT Pub. Date: Mar. 11, 2021

(65) Prior Publication Data
US 2022/0183635 A1 Jun. 16, 2022

(51) Int. Cl.
*A61B 5/00* (2006.01)
*G16H 30/20* (2018.01)
*G16H 50/20* (2018.01)

(52) U.S. Cl.
CPC .......... *A61B 5/7289* (2013.01); *A61B 5/7282* (2013.01); *G16H 30/20* (2018.01); *G16H 50/20* (2018.01)

(58) Field of Classification Search
CPC .... A61B 5/7289; A61B 5/7282; G16H 30/20; G16H 50/20
(Continued)

(56) References Cited

U.S. PATENT DOCUMENTS

2004/0077941 A1* 4/2004 Reddy .................. A61B 5/349
600/509
2005/0096543 A1 5/2005 Jackson et al.
(Continued)

FOREIGN PATENT DOCUMENTS

CN 101166460 A 6/2010
CN 101028187 A 7/2012
(Continued)

OTHER PUBLICATIONS

Bengel, Frank M., et al. "Cardiac positron emission tomography." Journal of the American College of Cardiology 54.1 (2009): 1-15.
(Continued)

*Primary Examiner* — Michael R Neff

(57) ABSTRACT

A system to generate images based on imaging data of a portion of a body and physiological event data associated with a physiological process of the body. The system is to identify a plurality of physiological cycles based on the physiological event data, determine a duration of each of the plurality of physiological cycles, determine a representative duration based on the durations of each of the plurality of physiological cycles, identify a first plurality of the plurality of physiological cycles based on a difference between the durations of the first plurality of physiological cycles and the representative duration, identify a second plurality of the plurality of physiological cycles different from the first plurality of the plurality of physiological cycles, determine a predetermined number of portions of each of the second plurality of the plurality of physiological cycles, accumulate imaging data acquired during respective portions of each of the second plurality of the plurality of physiological cycles to determine a set of accumulated imaging data for each of the predetermined number of portions, and generate a plurality of images, each of the plurality of images being
(Continued)

generated based on a respective one of the sets of accumulated imaging data.

20 Claims, 10 Drawing Sheets

(58) Field of Classification Search
USPC .......................................................... 382/128
See application file for complete search history.

(56) References Cited

U.S. PATENT DOCUMENTS

| | | |
|---|---|---|
| 2005/0203395 A1 | 9/2005 | Sui et al. |
| 2006/0264739 A1 | 11/2006 | Ariav et al. |
| 2007/0066881 A1 | 3/2007 | Edwards et al. |
| 2008/0170654 A1 | 7/2008 | Tkaczyk et al. |
| 2008/0300486 A1 | 12/2008 | Tirumalai et al. |
| 2009/0152471 A1 | 6/2009 | Rousso et al. |
| 2016/0015352 A1 | 1/2016 | Neocoil et al. |
| 2017/0039738 A1 | 2/2017 | Ziv et al. |

FOREIGN PATENT DOCUMENTS

| | | |
|---|---|---|
| CN | 101541232 A | 7/2013 |
| CN | 103200872 A | 7/2013 |
| JP | S6183987 A | 4/1986 |
| JP | H01299489 A | 12/1989 |
| JP | H05312958 A1 | 11/1993 |
| JP | 2016129662 A | 4/2020 |
| WO | 2011101752 A1 | 8/2011 |
| WO | 2013062049 A1 | 5/2013 |
| WO | 2021045760 A1 | 3/2021 |

OTHER PUBLICATIONS

Juarez-Orozco, Luis Eduardo, et al. "Phase analysis of gated PET in the evaluation of mechanical ventricular synchrony: A narrative overview." Journal of nuclear cardiology 26 (2019): 1904-1913.
Yahil, A. et al., "The Velocity Distribution of Galaxies in Clusters", The Astrophysical Journal, 214: 347-350, Jun. 1, 1977, The American Astronomical Society, 4 pages.
CT Physics: Cardiac CT (2014), http://xrayphysics.com/cardiac_ct.html#retrospective (accessed Nov. 11, 2021).
International Search Report for corresponding application No. PCT/US2019/049681, dated Dec. 11, 2019.

* cited by examiner

GATING OF MEDICAL IMAGING DATA

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

Detection of the emitted gamma rays occurs over a period of time, during which the body moves due to natural physiological processes such as respiration and heartbeat. Such movement can lead to blurred images, particularly in the abdominal, thoracic and cardiac regions. In order to address this movement, and in view of the cyclical nature of the movement, systems may identify the phase of the movement cycle during which image data was acquired and reconstruct an image for each phase based on its corresponding image data.

Cyclical body movement due to physiological processes is not perfectly uniform. Over a given period of time, cycles may differ in length, may terminate before fully complete, and/or may otherwise differ from a typical cycle. For such cycles, accurate identification of phases and corresponding image data may be difficult or impossible. The quality of phase-specific images reconstructed from such image data thereby suffers.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide retrospective gating of imaging data. Generally, imaging data is acquired over several physiological cycles, and the duration of each cycle is determined. Physiological cycles are identified whose duration deviates from that of a typical cycle. In some embodiments, cycles which are proximate to the identified cycles are also identified. The imaging data associated with the identified cycles is ignored and one or more images are reconstructed based on the imaging data which was acquired during the other cycles.

According to some embodiments, each of the other cycles is divided into an equal number of bins. The imaging data of one or more bins may be accumulated and reconstructed to generate an image corresponding to the one or more bins. For example, if the cycles are divided into four bins, the imaging data of each of the four bins may be accumulated and reconstructed to generate four images, each of which corresponds to one of the four bins.

Figure 1:
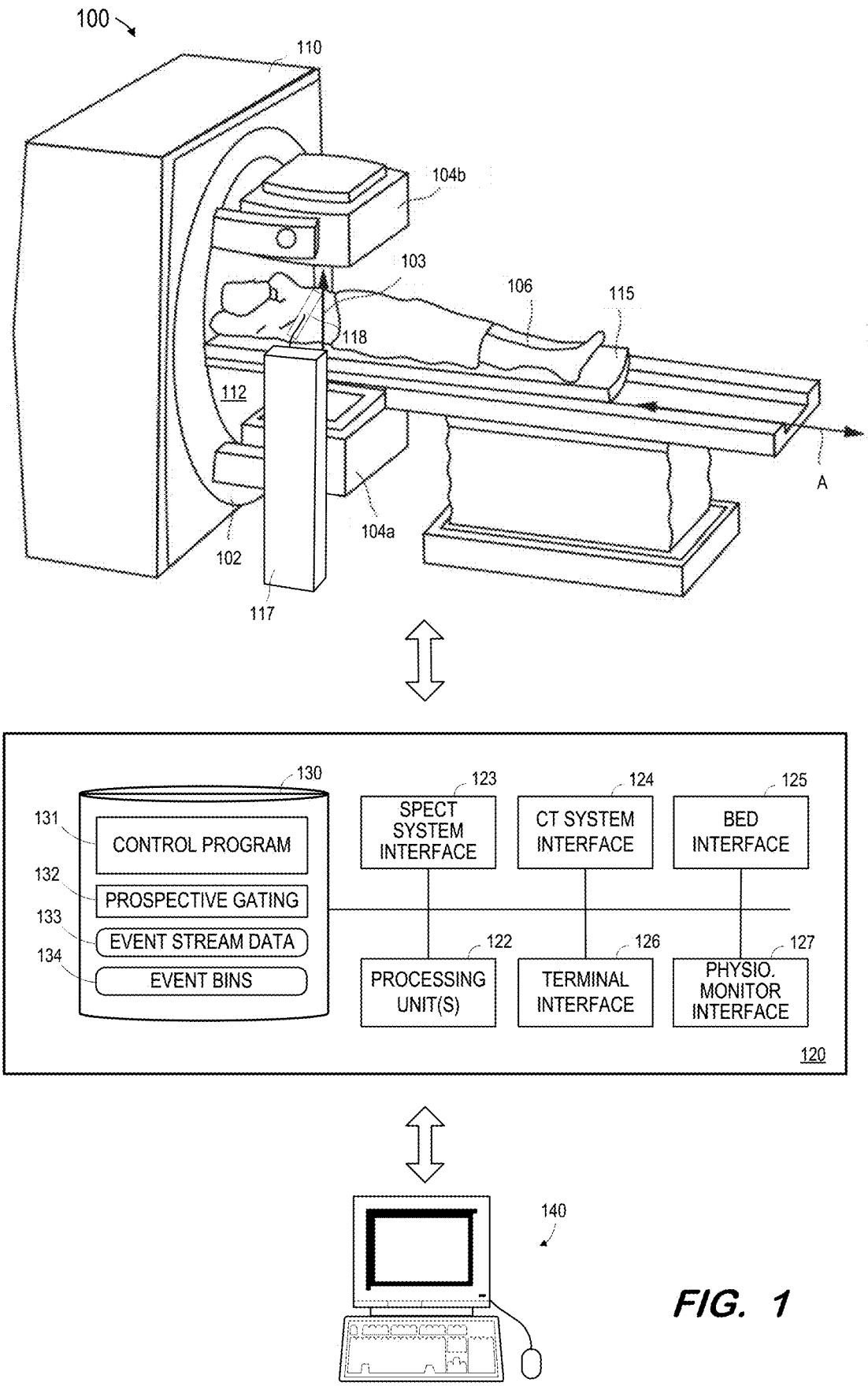
FIG. 1 illustrates an imaging system according to some embodiments.

FIG. 1 illustrates SPECT-CT system 100 to execute one or more of the processes described herein. Embodiments are not limited to system 100.

System 100 includes gantry 102 to which two or more gamma cameras 104a, 104b are attached, although any number of gamma cameras can be used. A detector within each gamma camera detects gamma photons 103 (i.e., emission data) emitted by a radiopharmaceutical within the body of patient 106 lying on bed 115. Bed 115 is slidable along axis-of-motion A. At respective bed positions (i.e., imaging positions), a portion of the body of patient 106 is positioned between gamma cameras 104a, 104b in order to capture emission data from that body portion.

System 100 also includes CT housing 110 including an X-ray imaging system (unshown) as is known in the art. Generally, and according to some embodiments, the X-ray imaging system acquires two-dimensional X-ray images of patient 106 before, during and/or after acquisition of emission data using gamma cameras 104a and 104b.

Physiological motion monitor 117 may comprise an electrocardiogram system coupled to sensor(s) 118 as is known in the art. Sensor(s) 118 may be attached to a patient as is known in the art to acquire a cardiac signal. In some embodiments, monitor 117 comprises a respiration monitor which senses a respiratory signal representing phases of breathing during nuclear image scanning. The signal(s) acquired by monitor 117 may be used as described above to separate acquired imaging data into bins which may represent respective phases of motion.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with SPECT system interface 123, bed interface 125, and monitor interface 127, control hardware elements to move a patient into bore 112 and, during the movement, control gamma cameras to rotate around bore 112 and to acquire two-dimensional emission data and physiological data of a body located in bore 112 at defined imaging positions during the rotation. The acquired data may be stored in memory 130 as event stream data 133.

Prospective gating program 132 may be executed to identify "good" physiological cycles and to bin the acquired SPECT data thereof as will be described below. The binned SPECT data may be stored in event bins 134, and SPECT images may be reconstructed therefrom.

Reconstructed SPECT images may be transmitted to terminal 140 via terminal interface 126. Terminal 140 may comprise a display device and an input device coupled to system 120. Terminal 140 may receive user input for controlling display of the data, operation of system 100, and/or the processing described herein. In some embodiments, terminal 140 is a separate computing device such as, but not limited to, a desktop computer, a laptop computer, a tablet computer, and a smartphone.

According to some embodiments, SPECT imaging data is subjected to motion correction and attenuation correction prior to reconstruction. The corrections may utilize CT imaging data acquired contemporaneously with the SPECT imaging data as is known in the art.

Each of component of system 100 may include other elements which are necessary for the operation thereof, as well as additional elements for providing functions other than those described herein. Although the embodiments described herein are related to SPECT imaging data, the described processes are applicable to any imaging modality, such as but not limited to PET, CT, and Magnetic Resonance Imaging (MRI).

Figure 2A:
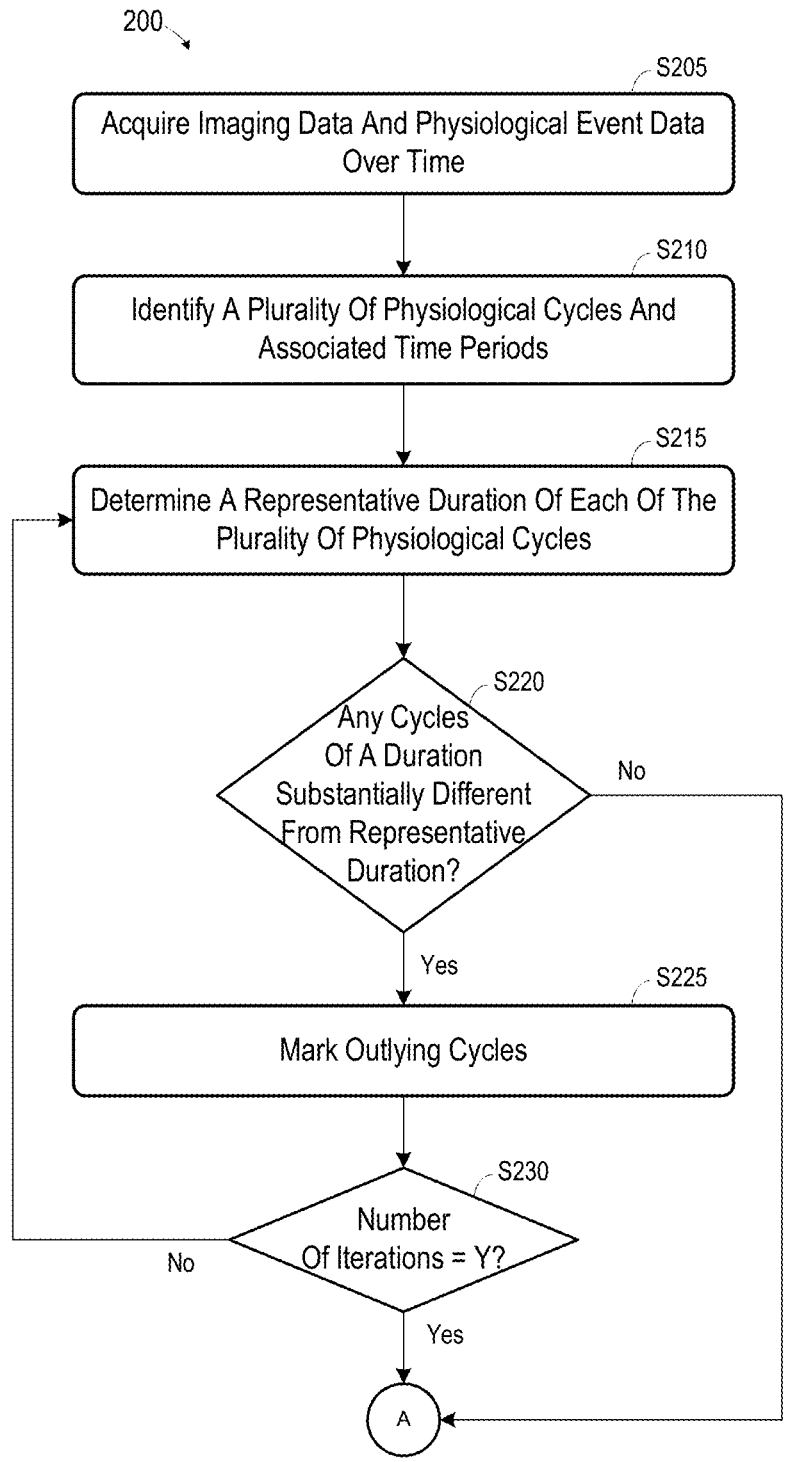
FIGS. 2A and 2B comprise a flow diagram of a process to gate image data according to some embodiments.
Figure 2B:
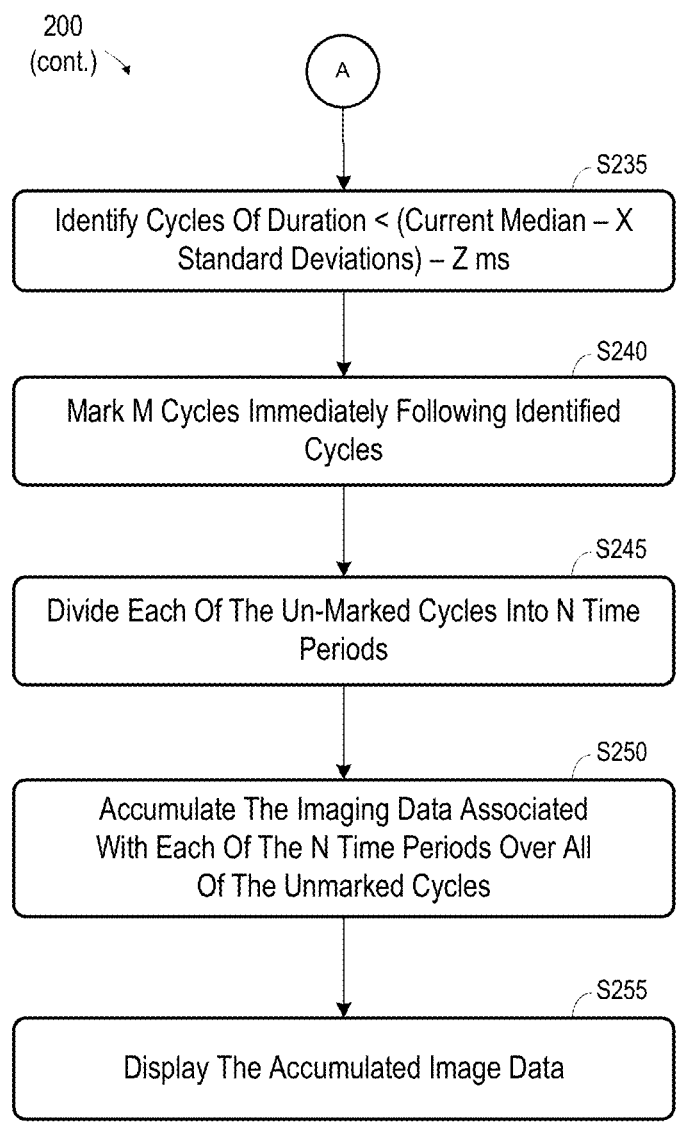

FIGS. 2A and 2B comprise a flow diagram of an image generation process according to some embodiments. Process 200 and other processes described herein may be executed using any suitable combination of hardware and software. Software program code embodying these processes may be stored by any non-transitory tangible medium, including a fixed disk, a volatile or non-volatile random-access memory, a DVD, a Flash drive, or a magnetic tape. Embodiments are not limited to the examples described below.

Initially, at S205, imaging data and physiological event data are acquired over time. The present example will be described in the context of a SPECT system, therefore S205 is preceded by introduction of a suitable radiopharmaceutical to a patient in any suitable manner, as is known in the art. Also in the present example, the physiological event data is cardiac event data as represented by an electrocardiogram (ECG) signal.

Figure 3:
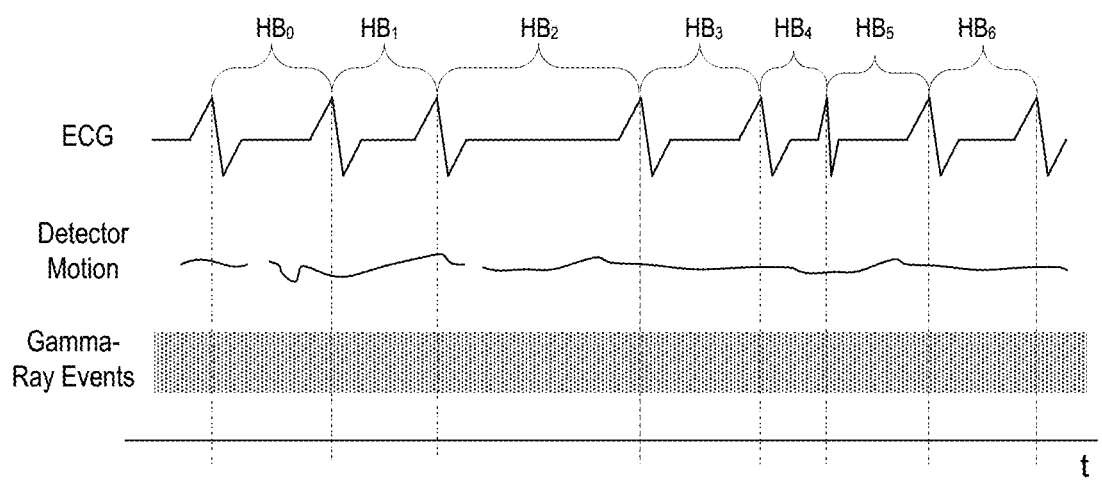
FIG. 3 illustrates image data and physiological data acquired according to some embodiments.

The imaging data and physiological event data may be acquired and electronically represented in any format that is or becomes known. FIG. 3 illustrates an example ECG signal which may be acquired at S205. Also depicted are signals representing gamma ray events and detector motion events acquired over time. These events may comprise list mode data as is known in the art. Embodiments are not limited to acquisition of the depicted signals. In some embodiments, each signal is combined into a single event stream including ECG events (e.g., detection of an R-wave), detector motion events, gamma-ray events and periodic time markers (e.g., every 1 ms).

At S210, a plurality of physiological cycles and associated time periods are identified from the acquired data. For example, a particular physiological cycle of interest may include an event which marks the beginning (or any other phase) of the cycle. In the case of a heartbeat cycle, it may be assumed that the peak of the R-wave of an ECG signal marks a beginning of the cycle.

In this regard, the ECG signal of FIG. 3 may be evaluated at S210 to identify heartbeat cycles $HB_0$ through $HB_6$. The time periods associated with each heartbeat cycle are denoted by the vertical dashed lines of FIG. 3. As shown, each time period is also associated with corresponding detector motion data and gamma-ray event data.

A representative duration of each of the plurality of physiological cycles under consideration is determined at S215. For example, a duration of each of the identified cycles is determined and a median duration is calculated based on all of the determined durations. Embodiments may utilize any other representative characterization of the durations, such as but not limited to the mean.

Figure 4:
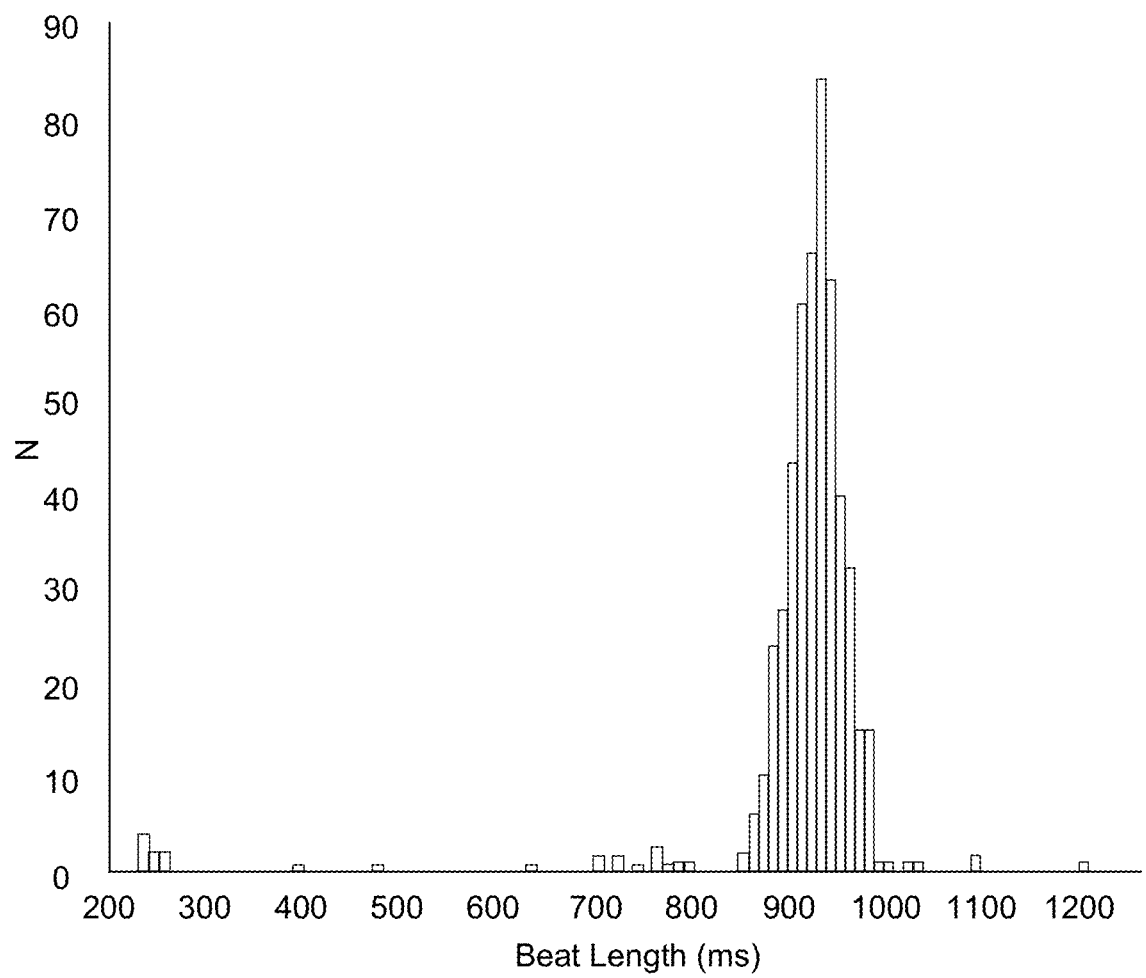
FIG. 4 is a histogram of heartbeat period lengths according to some embodiments.
Figure 5:
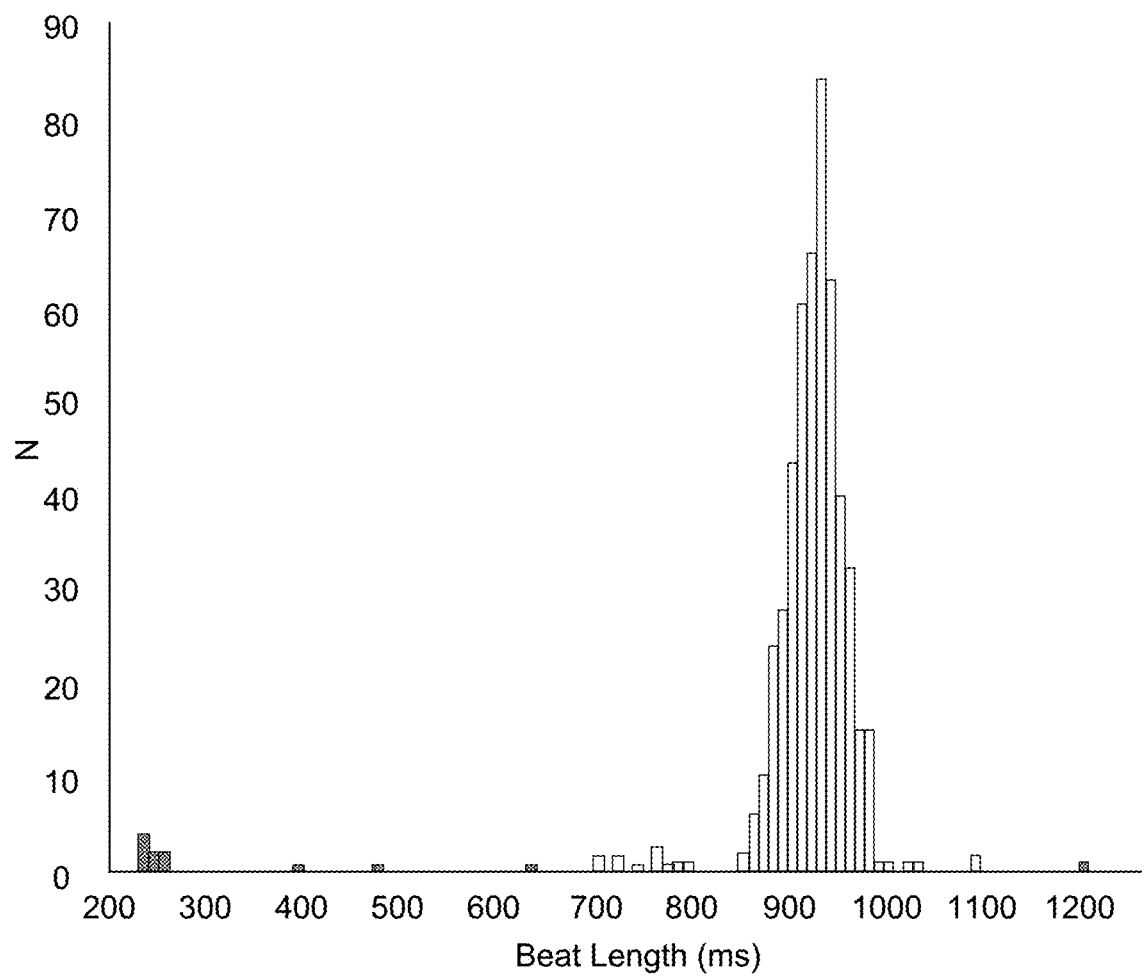
FIG. 5 is a histogram of heartbeat period lengths depicting outlier heartbeats identified according to some embodiments.

At S220, it is determined whether any of the identified cycles is of a duration which differs substantially from the representative duration. For example, S220 may comprise a determination of whether any of the identified cycles is of a duration greater than a prespecified number (e.g., 3) of standard deviations from a median duration. If so, these "outlying" cycles are marked, or otherwise identified, at S225. FIG. 4 is a histogram according to some embodiments, which plots cycle durations against number of cycles. According to the FIG. 4 example, most of the identified cycles are of duration between 850 ms and 1000 ms. The shaded bars of FIG. 5 denote cycles which were identified as outlying at S220 and marked at S225.

Flow then proceeds to S230 to determine whether the number of executed iterations of S215-S225 is equal to a pre-specified maximum number of iterations (e.g., 3). If not, flow returns to S215 to determine a representative duration of each of the cycles under consideration. Continuing the present example, the cycles under consideration are those cycles which have not been marked at S225 (i.e., the cycles corresponding to the unshaded bars of FIG. 5).

Figure 6:
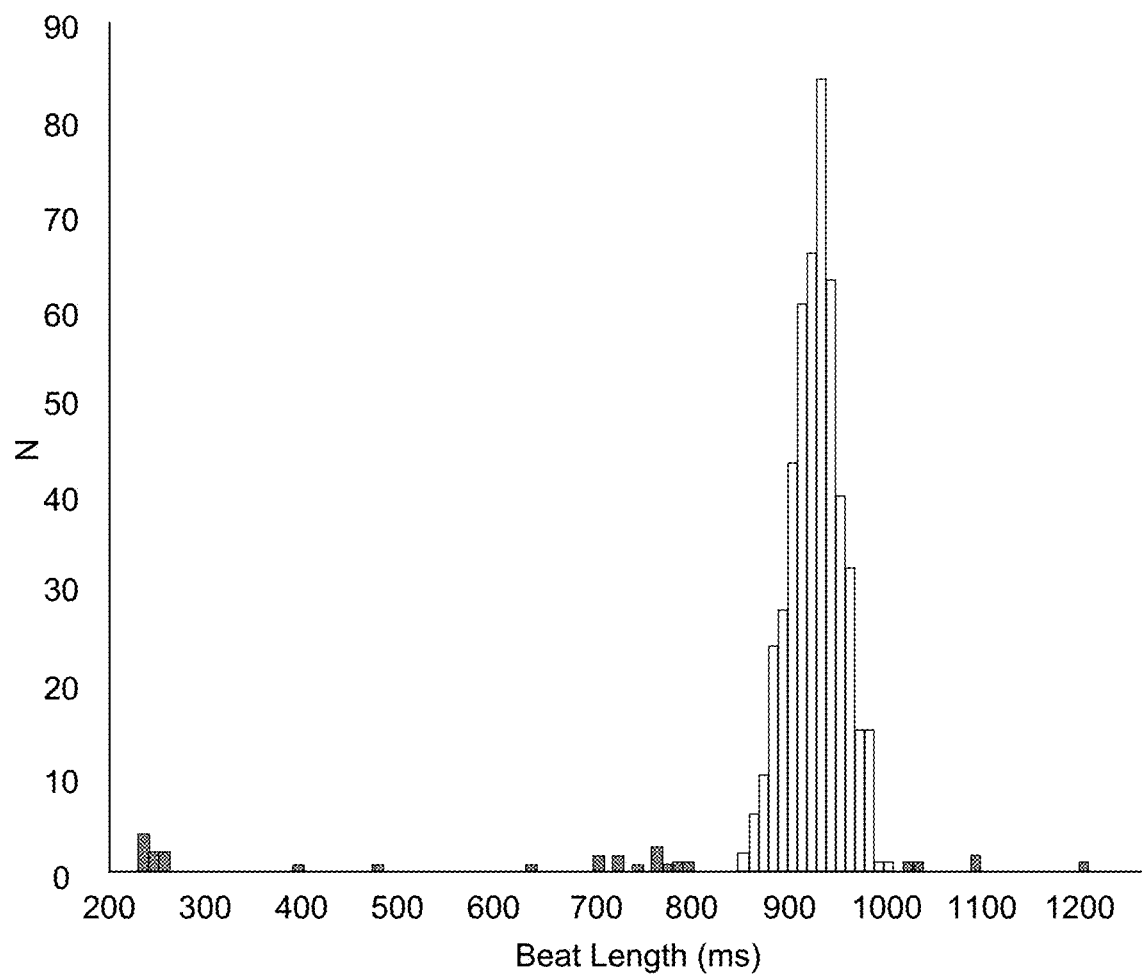
FIG. 6 is a histogram of heartbeat period lengths depicting outlier heartbeats identified according to some embodiments.

Flow then proceeds as described above, to determine whether any of the identified cycles is of a duration substantially different from the (new) representative duration at S220, and, if so, to mark the outlying cycles at S225. FIG. 6 illustrates the histogram of the present example, in which additional bars are shaded as a result of the second iteration of S215-S225.

During the above iterative process, flow exits from S220 to S235 if it is determined that none of the cycles currently under consideration are of a duration substantially different from the current representative duration. Flow also exits from S230 to S235 if it is determined that the number of executed iterations is equal to the pre-specified maximum number of iterations. For purposes of the present example, it will be assumed that flow exits to S235 after the above-described two iterations.

At S235, cycles are identified which are more than a pre-specified number of milliseconds less than the current representative duration minus a pre-specified number of standard deviations. Due to the particular calculation at S235, the identified cycles will have been previously marked at S225. S235 is intended to identify cycles which may be associated with a pre-ventricular compression (PVC). For example, cycle $HB_4$ of FIG. 3 may be associated with a PVC. Embodiments may therefore employ any suitable calculation at S235.

Figure 7:
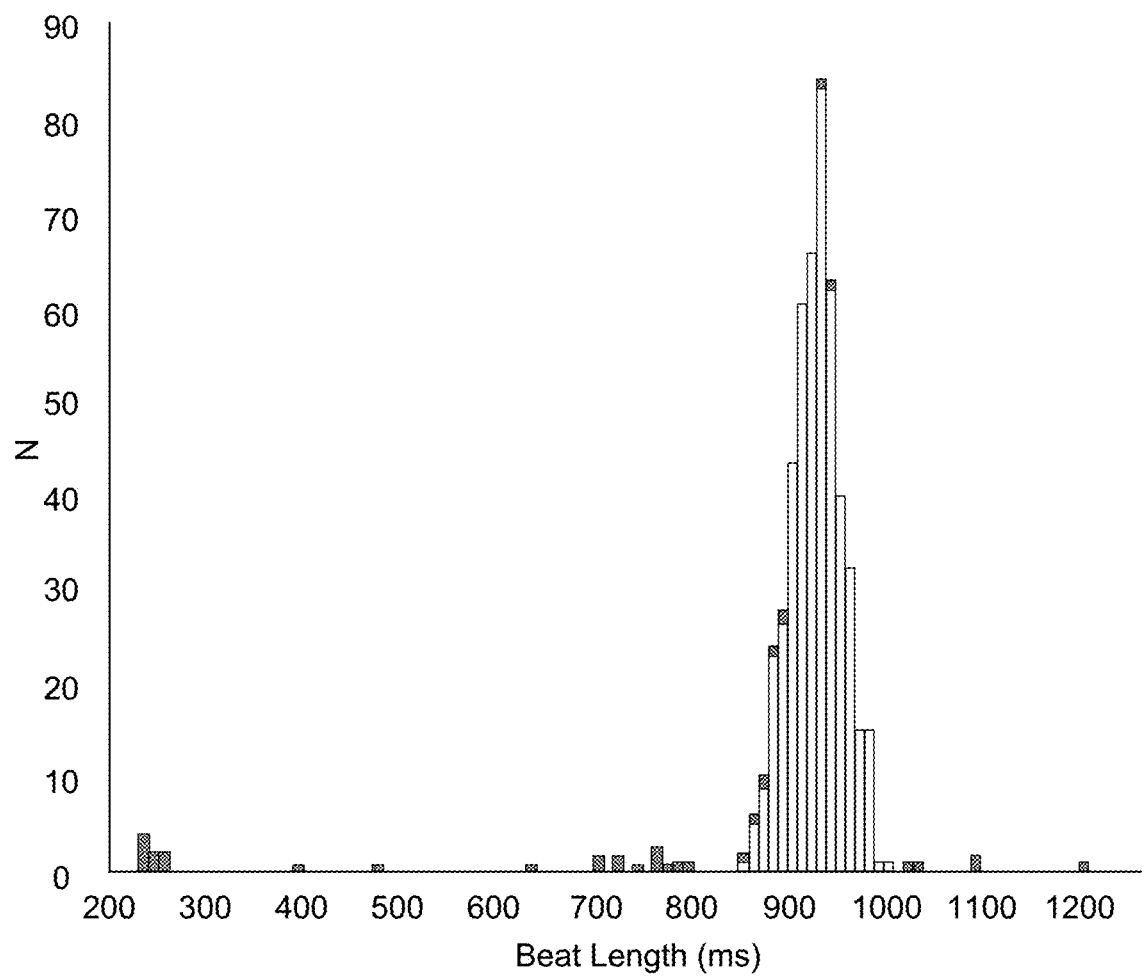
FIG. 7 is a histogram of heartbeat period lengths depicting outlier heartbeats, pre-ventricular compressions and heartbeats following pre-ventricular compressions identified according to some embodiments.

At S240, a predetermined number of cycles which follow each cycle identified at S235 are marked. S240 is intended to mark cycles which may be atypical due to their temporal proximity to a PVC. With reference to FIG. 3, cycle $HB_5$ is marked at S240 if the predetermined number is 1, and cycles $HB_5$ and $HB_6$ are marked if the predetermined number is 2. FIG. 7 illustrates the additional cycles marked at S240, which have durations between 850 ms and 1000 ms.

Upon reaching S245, the originally-identified plurality of cycles now consist of marked cycles and un-marked cycles. Each of the un-marked cycles is divided into a plurality of time periods at S245.

Figure 8:
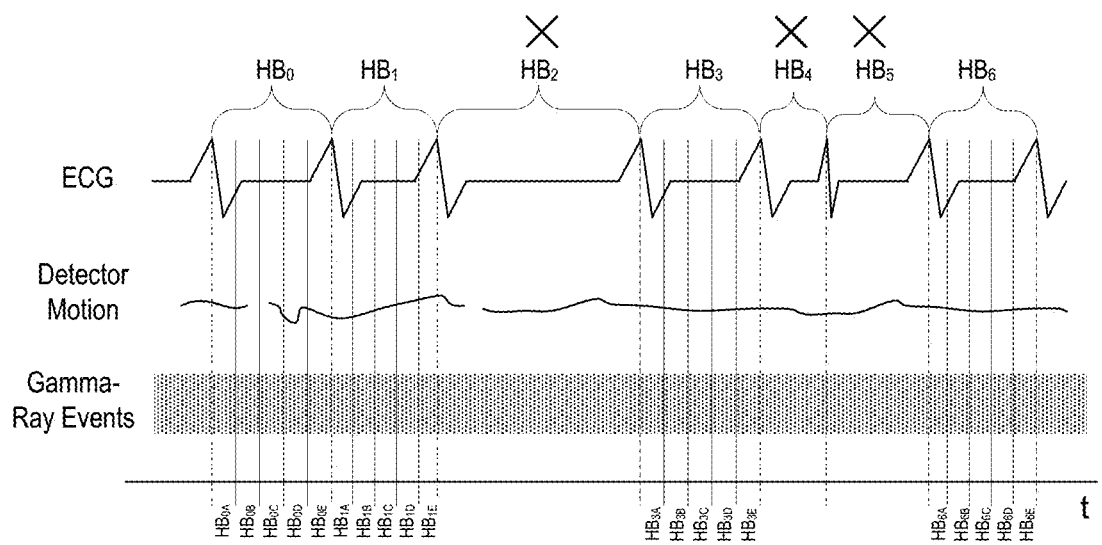
FIG. 8 illustrates binning of imaging data according to some embodiments.

FIG. 8 shows the FIG. 3 cycles, in which heartbeat cycle $HB_2$ was marked at S225 due to its long duration, heartbeat cycle $HB_4$ was marked at S225 due to its short duration, and heartbeat cycle $HB_5$ was marked at S240 due to previous short heartbeat cycle $HB_4$.

Each of unmarked heartbeat cycles $HB_0$, $HB_1$, $HB_3$, and $HB_6$ has been divided into five bins at S245. Embodiments are not limited to any particular number of bins, but some implementations may use 8 or 16 bins in keeping with the traditional number of bins in cardiac imaging. Since the cycles are evenly divided, all bins of any one cycle are equal in duration. That is, bins $HB_{0A}$ through $HB_{0E}$ are all of the same duration. However, since the total duration of each unmarked cycle may differ from one another, the duration of a bin of a first cycle (i.e., one-fifth of the first cycle) may differ from the duration of a bin of a second cycle (i.e., one-fifth of the second cycle).

It may be roughly assumed that respective bins (e.g., all $HB_{xA}$ bins) are associated with a same phase of the heartbeat cycle. Each bin is associated with all imaging data received during the time duration (or phase) corresponding to the bin. Accordingly, at S250, the imaging data associated with each of the predetermined time periods (i.e., the bins) of the unmarked cycles is accumulated. For example, all of the imaging data acquired during bins $HB_{0A}$, $HB_{1A}$, $HB_{3A}$, $HB_{6A}$ is accumulated into a single set of imaging data associated with bin A, while all of the imaging data acquired during bins $HB_{0B}$, $HB_{1B}$, $HB_{3B}$, $HB_{6B}$ is accumulated into a single set of imaging data associated with bin B.

The accumulated image data is displayed at S255. For example, an image may be generated by applying known reconstruction techniques to the accumulated imaging data associated with bin A. The thusly-generated image may be considered as representing the phase of motion associated with bin A. Similarly, respective images may be generated based on the accumulated imaging data associated with each other bin, where each image represents the phase of motion associated with its bin. In some embodiments, an image may be generated based on the accumulated imaging data of more than one bin, or of all the bins (i.e., a composite image).

Figure 9:
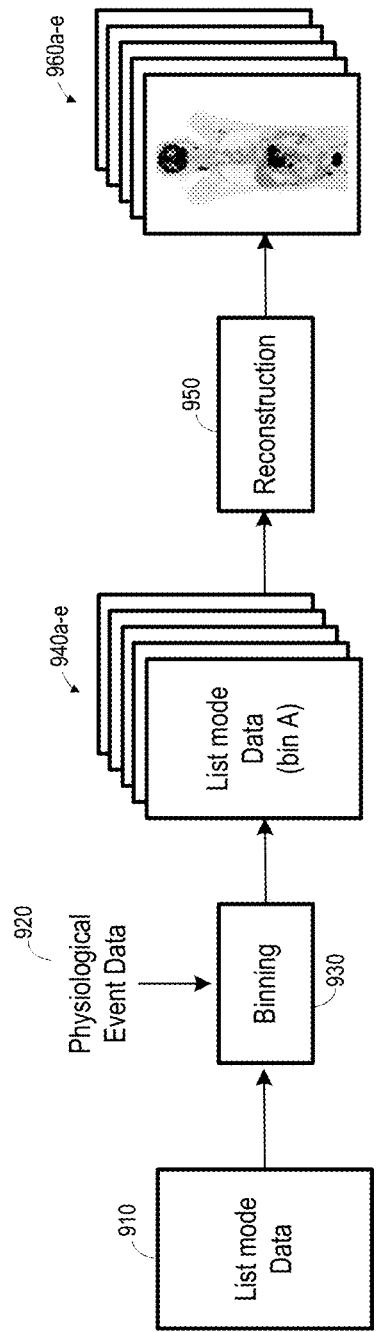
FIG. 9 illustrates a system for binning and reconstructing imaging data according to some embodiments.

FIG. 9 illustrates the accumulation of imaging data associated with bins representing each of a plurality of motion phases and generation of images based thereon according to some embodiments of S250 and S255.

In some embodiments, imaging data 910 is acquired at S205 in "list mode", in which each detected gamma-ray is associated with a detection time as well as other detected values which enable location of the emission event. Binning component 930 receives list mode data 910 and physiological event data 920. Physiological event data 920 may indicate, directly or indirectly, a phase of motion in which the imaged region resided at various times throughout acquisition of list mode data 910.

Binning component 930 may execute S210 through S250 as described above, resulting in binned data 940a-e. Binned data 940a-e represents imaging data separated into five bins, each of which represents a portion of a physiological cycle. Embodiments are not limited to any particular number of bins/portions. The imaging data of each bin represents gamma-ray detections which occurred during the portion of the cycle which is associated with the bin.

Reconstruction component 950 generates an image based on each of binned data 940a-e, resulting in binned images 960a-e. Each of binned images 960a-e may therefore represent the imaged region as positioned during a portion of a physiological cycle associated with a particular bin.

Each functional component described herein may be implemented at least in part in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    an imaging device to:
        acquire imaging data of a portion of a body;
    a physiological monitoring device to:
        acquire physiological event data associated with a physiological process of the body while the imaging device acquires first imaging data; and
    a processing system to:
        identify, based on the physiological event data, a plurality of physiological cycles which occurred while the imaging device acquired the first imaging data;
        determine a duration of each of the identified plurality of physiological cycles;
        determine a representative duration based on the determined durations of each of the identified plurality of physiological cycles;
        identify a first plurality of the plurality of physiological cycles which were of a duration substantially different from the representative duration, and a second plurality of the plurality of physiological cycles which are different from the first plurality of the plurality of physiological cycles;
        divide each of the second plurality of the plurality of physiological cycles into a plurality of time periods;
        for each of the plurality of time periods, determine the first imaging data acquired during a time period of each of the second plurality of the plurality of physiological cycles to determine a set of imaging data for the time period; and
        for each of the plurality of time periods, generate an image based on the set of imaging data determined for a time period.

2. A system according to claim 1, wherein identification of the first plurality of the plurality of physiological cycles comprises:
    identification of a first plurality of the plurality of physiological cycles of a duration greater than a predetermined number of standard deviations from the representative duration.

3. A system according to claim 2, wherein the representative duration is based on a median of the durations of each of the plurality of physiological cycles.

4. A system according to claim 1, wherein identification of the first plurality of the plurality of physiological cycles comprises:
    identification of a third plurality of the plurality of physiological cycles of a duration greater than a predetermined number of standard deviations from the representative duration;
    determination of a second representative duration of the third plurality of the plurality of physiological cycles; and
    identification of the first plurality of the plurality of physiological cycles of a duration greater than the predetermined number of standard deviations from the second representative duration.

5. A system according to claim 4, wherein the representative duration is based on a median of the durations of each of the plurality of physiological cycles, and
wherein the second representative duration is based on a median of the durations of each of the third plurality of the plurality of physiological cycles.

6. A system according to claim 4, the processing system further to:
identify a fourth plurality of physiological cycles, each of the fourth plurality of physiological cycles immediately following ones of the third plurality of the plurality of physiological cycles,
wherein the second plurality of physiological cycles do not include any of the fourth plurality of physiological cycles.

7. A system according to claim 1, the processing system further to:
identify a third plurality of physiological cycles, each of the third plurality of physiological cycles immediately following ones of the first plurality of the plurality of physiological cycles,
wherein the second plurality of physiological cycles do not include any of the third plurality of physiological cycles.

8. A method comprising:
acquiring imaging data of a portion of a body;
while acquiring the imaging data, acquiring physiological event data associated with a physiological process of the body;
identifying a plurality of physiological cycles which occurred while the imaging data was acquired based on the physiological event data;
determining a duration of each of the identified plurality of physiological cycles;
determining a representative duration based on the determined durations of each of the identified plurality of physiological cycles;
identifying a first plurality of the plurality of physiological cycles based on a difference between the durations of the first plurality of physiological cycles and the representative duration;
identifying a second plurality of the plurality of physiological cycles different from the first plurality of the plurality of physiological cycles;
determining a plurality of portions of each of the second plurality of the plurality of physiological cycles;
for each of the plurality of portions, determining the imaging data acquired during a portion of each of the second plurality of the plurality of physiological cycles to determine a set of imaging data for the portion; and
for each of the plurality of portions, generating an image based on the set of imaging data determined for a portion.

9. A method according to claim 8, wherein identifying the first plurality of the plurality of physiological cycles comprises:
identifying a first plurality of the plurality of physiological cycles of a duration greater than a predetermined number of standard deviations from the representative duration.

10. A method according to claim 9, wherein the representative duration is based on a median of the durations of each of the plurality of physiological cycles.

11. A method according to claim 8, wherein identification of the first plurality of the plurality of physiological cycles comprises:
identification of a third plurality of the plurality of physiological cycles of a duration greater than a predetermined number of standard deviations from the representative duration;
determination of a second representative duration of the third plurality of the plurality of physiological cycles; and
identification of the first plurality of the plurality of physiological cycles of a duration greater than the predetermined number of standard deviations from the second representative duration.

12. A method according to claim 11, wherein the representative duration is based on a median of the durations of each of the plurality of physiological cycles, and
wherein the second representative duration is based on a median of the durations of each of the third plurality of the plurality of physiological cycles.

13. A method according to claim 11, further comprising:
identifying a fourth plurality of physiological cycles, each of the fourth plurality of physiological cycles immediately following ones of the third plurality of the plurality of physiological cycles,
wherein the second plurality of physiological cycles do not include any of the fourth plurality of physiological cycles.

14. A method according to claim 8, further comprising:
identifying a third plurality of physiological cycles, each of the third plurality of physiological cycles immediately following ones of the first plurality of the plurality of physiological cycles,
wherein the second plurality of physiological cycles do not include any of the third plurality of physiological cycles.

15. A system to generate images based on imaging data of a portion of a body and physiological event data associated with a physiological process of the body, the system to:
identify, based on the physiological event data, a plurality of physiological cycles which occurred during acquisition of the imaging data;
determine a duration of each of the plurality of physiological cycles;
determine a representative duration based on the durations of each of the plurality of physiological cycles;
identify a first plurality of the plurality of physiological cycles based on a difference between the durations of the first plurality of physiological cycles and the representative duration;
identify a second plurality of the plurality of physiological cycles different from the first plurality of the plurality of physiological cycles;
determine a plurality of time periods of each of the second plurality of the plurality of physiological cycles;
for each of the plurality of time periods, accumulate imaging data acquired during a time period of each of the second plurality of the plurality of physiological cycles to determine a set of accumulated imaging data for the time period; and
generate a plurality of images, each of the plurality of images being generated based on a respective one of the sets of accumulated imaging data.

16. A system according to claim 15, wherein identification of the first plurality of the plurality of physiological cycles comprises:

identification of a first plurality of the plurality of physiological cycles of a duration greater than a predetermined number of standard deviations from the representative duration.

17. A system according to claim 16, wherein the representative duration is based on a median of the durations of each of the plurality of physiological cycles.

18. A system according to claim 15, wherein identification of the first plurality of the plurality of physiological cycles comprises:
   identification of a third plurality of the plurality of physiological cycles of a duration greater than a predetermined number of standard deviations from the representative duration;
   determination of a second representative duration of the third plurality of the plurality of physiological cycles; and
   identification of the first plurality of the plurality of physiological cycles of a duration greater than the predetermined number of standard deviations from the second representative duration.

19. A system according to claim 18, wherein the representative duration is based on a median of the durations of each of the plurality of physiological cycles, and
   wherein the second representative duration is based on a median of the durations of each of the third plurality of the plurality of physiological cycles.

20. A system according to claim 18, further to:
   identify a fourth plurality of physiological cycles, each of the fourth plurality of physiological cycles immediately following ones of the third plurality of the plurality of physiological cycles,
   wherein the second plurality of physiological cycles do not include any of the fourth plurality of physiological cycles.

* * * * *